United States Patent [19]

Silka et al.

[11] Patent Number: 4,577,764
[45] Date of Patent: Mar. 25, 1986

[54] WIRE RACK FOR PROCESSING HARD CONTAINER SYSTEMS IN WASHING-STERILIZERS

[75] Inventors: John L. Silka, Union City; Gerald L. Yeaney, Erie, both of Pa.

[73] Assignee: American Sterilizer Company, Erie, Pa.

[21] Appl. No.: 629,168

[22] Filed: Jul. 9, 1984

[51] Int. Cl.$^4$ ............................................. A47G 19/08
[52] U.S. Cl. ........................................ 211/41; 211/181
[58] Field of Search ................ 211/41, 181, 71, 30; 312/128, 273; D32/58, 55, 59, 3

[56] References Cited

U.S. PATENT DOCUMENTS

| | | | |
|---|---|---|---|
| D. 181,365 | 11/1957 | Miller | 211/41 X |
| 1,172,799 | 2/1916 | Hormes | 211/30 X |
| 2,159,365 | 5/1939 | Barrie | 211/41 X |
| 2,440,507 | 4/1948 | Geralds | 211/41 X |
| 2,655,267 | 10/1953 | Planeta | 211/41 X |
| 2,697,525 | 12/1954 | Breneman | 211/41 |
| 2,841,288 | 7/1958 | Field et al. | 211/41 |
| 2,864,509 | 12/1958 | Watral | 211/41 |
| 2,889,054 | 6/1959 | Wheeler | 211/181 X |
| 3,169,641 | 2/1965 | Chapman | 211/41 X |

FOREIGN PATENT DOCUMENTS

| | | | |
|---|---|---|---|
| 754268 | 8/1956 | United Kingdom | 211/41 |
| 1469925 | 4/1977 | United Kingdom | 211/41 |

*Primary Examiner*—J. Franklin Foss
*Assistant Examiner*—Blair M. Johnson
*Attorney, Agent, or Firm*—Robert D. Yeager; Christine R. Ethridge

[57] ABSTRACT

An improved rack for holding first or second containers in washing and/or sterilizing apparatus, where the containers include a deep bottom portion and a shallow lid which, together with the bottom portion defines an enclosed chamber, and an intermediate portion for insertion into the chamber. The improved rack includes a rigid rectangular frame defining an opening and having a substantially rectangular diagonal member and two skewed square diagonal members on each side of the rectangle, a first set of wire components disposed on the lengths of the frame for supporting the bottom portions in an inverted position spanning at least a portion of the opening, a second set of wire components disposed on the diagonals for supporting the intermediate portions in a substantially vertical position, and a third set of wire components disposed on the frame for supporting the lids in a substantially obtusely angular position relative to the frame.

9 Claims, 12 Drawing Figures

WIRE RACK FOR PROCESSING HARD CONTAINER SYSTEMS IN WASHING-STERILIZERS

BACKGROUND OF THE INVENTION

1. Field of the Invention

The present invention relates to wire racks for holding containers in washing and/or sterilizing apparatus, and more particularly, to an improved wire rack for holding at least one of either a large or small rigid container having a deep bottom portion, a lid and an intermediate portion.

2. Description of the Prior Art

Hospitals have for a long time used muslin wraps to enclose surgical instruments during sterilization and during the transport and storage of instruments following sterilization. Recently, specially designed rigid containers have replaced the muslin wrap as the enclosure of choice for use during the sterilization of surgical instruments and other health care related items. The containers include bottom portions of varying depths for holding the instruments and other items, lids, which, together with the bottom portions define an enclosed space, and an intermediate portion for insertion into the space. The intermediate portions may be either filter plates or valve assembly plates which protect the instruments or other items being sterilized against reinfection during transport and storage. The containers are available in small and large sizes for accommodating different instrument loads.

Problems have been encountered during cleaning and during the first phase of sterilizing the containers. Conventional racks used to hold the containers do not permit the container portions to be positioned for efficient washing and/or sterilizing. The surfaces of the portions of the containers are not evenly accessible by fluid injected into the washing and/or sterilizing apparatus. Liquids are sometimes retained in the container portions because of the positioning necessitated by the conventional racks.

In addition, the rigid container surfaces are subject to mechanical abuse, such as denting and abrasion, from contact with other rigid surfaces during the washing and/or sterilizing.

Accordingly, there is a need for a rack for holding either the small or large containers having deep bottom portions, lids and intermediate portions, in washing and/or sterilizing apparatus which permits the container portions to be positioned for substantially unobstructed exposure of all surfaces of the containers to the fluid injected into the apparatus. There is a further need for such a rack which will permit the container portions to be positioned to avoid mechanical abuse by being maintained in a spaced relationship relative to the other portions. Finally, there is a need for such a rack which will permit such positioning within the space available in conventional washing and/or sterilizing apparatus.

SUMMARY OF THE INVENTION

The present invention provides an improved rack for holding at least one of either a first sized or a second, differently sized rigid container within a basket of a predetermined size, which also holds a tray of instruments, for insertion into apparatus for washing and/or sterilizing, where fluid is directed toward the containers through the basket from at least the bottom of the apparatus. The containers include a deep bottom portion defining a chamber, a shallow lid for enclosing the chamber, and an intermediate portion for insertion into the chamber. The tray of instruments can be subsequently inserted into the chamber.

The improved rack includes a rigid, preferably rectangular, frame lying in a horizontal plane relative to the bottom of the apparatus and defining an opening. The frame may have such a bisecting transverse axis that two halves are defined thereby, and may have a first substantially diagonal member crossing the rectangular frame and two second skewed diagonal members, one of the second diagonal members crossing one of the halves. The improved rack also includes a first set of wire components supported by the frame end preferably disposed along each length of the rectangular frame, and positioned to support at least one of either of the first or second container bottom portions in such an inverted position in a spaced relationship relative to the frame over at least a portion of the opening that the chamber can be exposed to the fluid directed from the bottom of the apparatus and can be positioned to prevent the retention of fluid within the bottom portions.

The improved rack also includes a second set of wire components supported by the frame and preferably disposed along each of the first and second diagonal members. The second set of components are positioned to support the intermediate portions in such a substantially vertical position relative to the plane in a spaced relationship relative to the bottom portion when the bottom portion is supported by the first set of components that the retention of fluid in the intermediate portions is substantially prevented. In the preferred embodiment, the first diagonal member has disposed thereon components of the second set for supporting the intermediate portions of either the first or second containers and each of the second diagonal members has disposed thereon components of the second set for supporting the intermediate portions of a second container.

The improved rack also includes a third set of wire components supported by the frame and preferably disposed along the frame. The third set of components is positioned to support at least one of either the first or second container lids in such a substantially obtusely angular position relative to the frame that the retention of fluids in the lids can be substantially prevented. The third set of components is positioned to support the lids in such a spaced relationship relative to the bottom portions and the intermediate portions when those portions are supported by the first and second sets of components that the direction of the fluid from the bottom of the apparatus toward the chambers and the intermediate portions is unobstructed by the lids.

Each of the components of the first set has two legs and a cross member therebetween, the legs being substantially vertical relative to the plane and the cross member being substantially horizontal relative to the legs. Each leg has a first end connected to one length of the frame and a second opposing end having such an upwardly extending section for contacting the bottom portions that the cross member is maintained in a spaced relationship relative to the bottom portions when the bottom portions are supported by the first set components.

Each of the second set components preferably has a first support member and a second support member for maintaining an intermediate portion therebetween. At least one of the support members may have a first means for maintaining the intermediate portion in a spaced relationship relative to the diagonal members. The components of the second set on the second diagonal members may also include two third support members for maintaining the intermediate portion of a first container between the first and second support members. Each of the third support members has a second means for maintaining the intermediate portion in a spaced relationship relative to the second diagonal member.

Each of the components of the third set has a fourth support member for maintaining the lid in a spaced relationship relative to the bottom portions and the intermediate portions when the bottom portions and intermediate portions are supported by the first and second sets of components, respectively, and a fifth support member having at least two extended fingers connected to the frame for supporting the lids in the substantially obtusely angular position.

The rack is preferably proportioned to hold either two second containers, each of which spans one of the halves, or one first container spanning the opening.

BRIEF DESCRIPTION OF THE DRAWINGS

The following detailed description of the preferred embodiment can better be understood if reference is made to the drawings in which.

DETAILED DESCRIPTION OF THE PREFERRED EMBODIMENT

Figure 1:
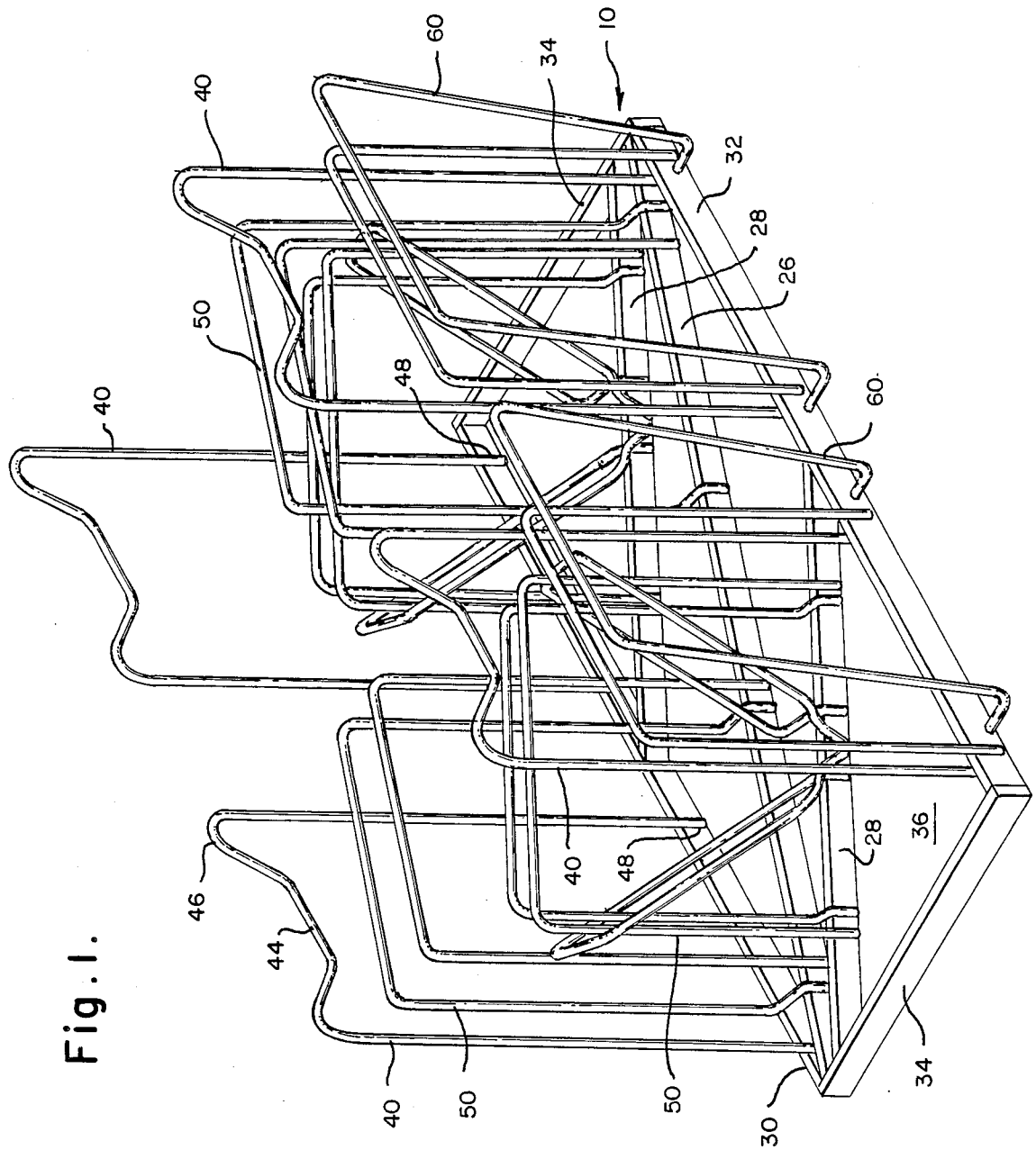
FIG. 1 is an isometric view of the preferred embodiment of the rack.
Figure 2:
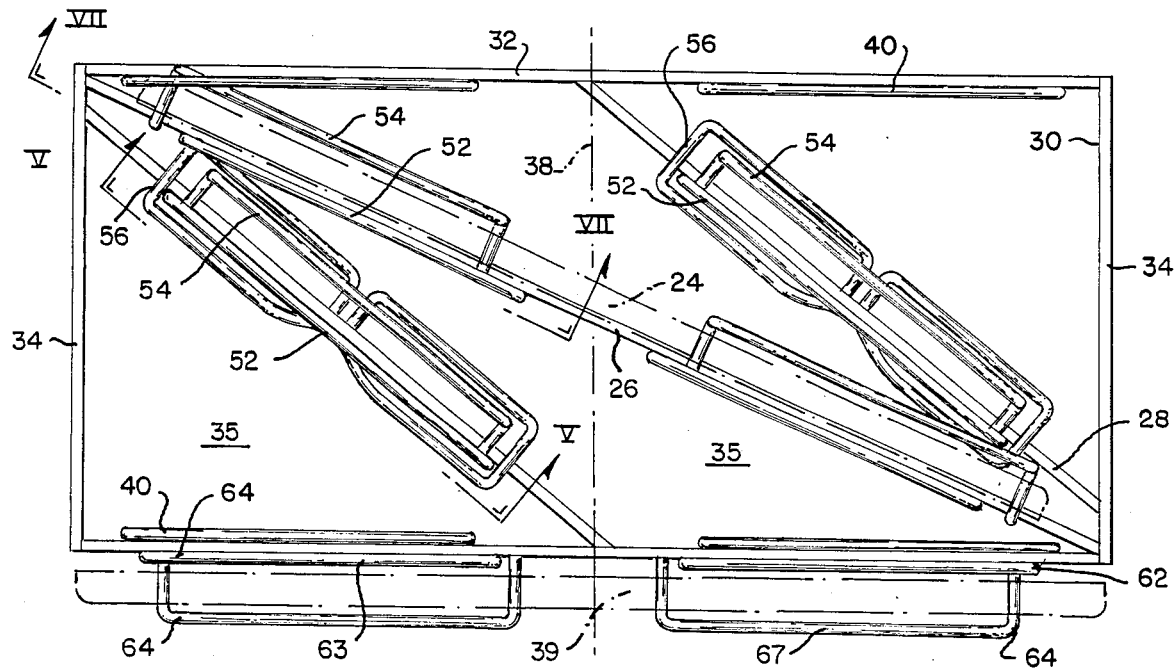
FIG. 2 is a top plan view of the rack shown in FIG. 1.
Figure 3:
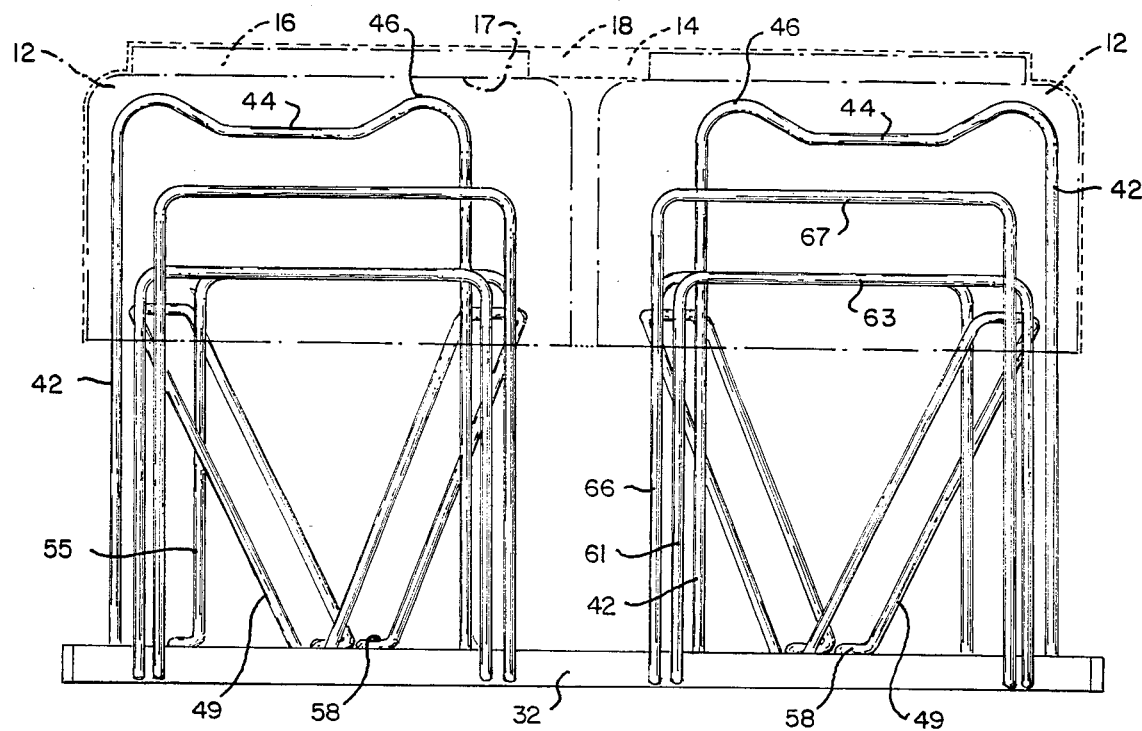
FIG. 3 is a front elevational view of the rack of FIG. 2.
Figure 4:
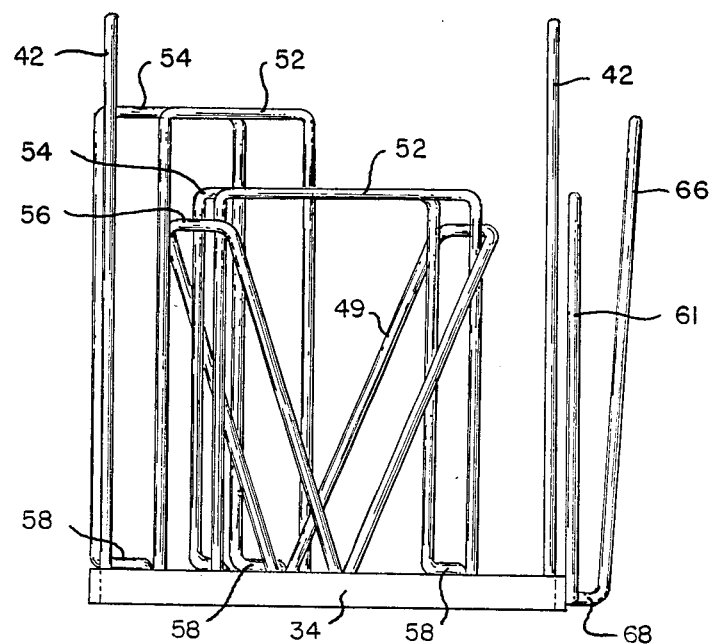
FIG. 4 is an end elevational view of the rack of FIG. 3 viewed from the left thereof.
Figure 5:
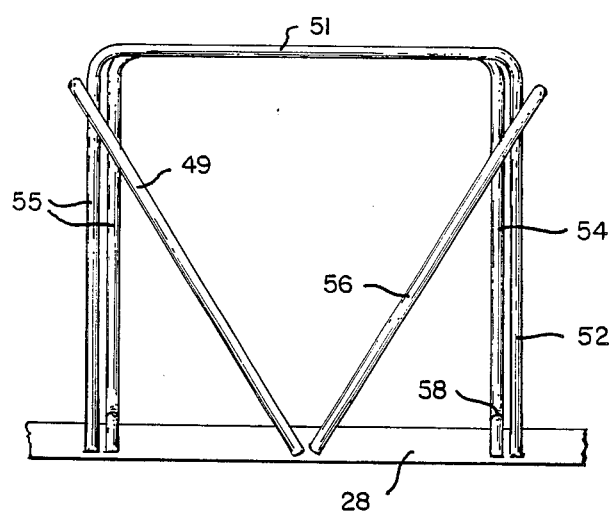
FIG. 5 is a view of a portion of the rack taken along the line V—V of FIG. 2.
Figure 6:
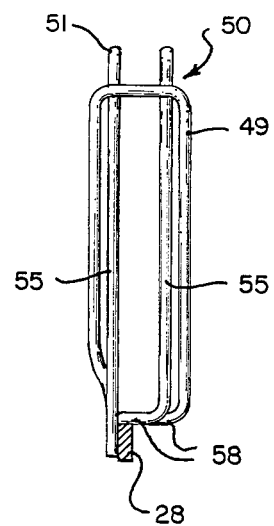
FIG. 6 is an end elevational view of the rack shown in FIG. 5 viewed from the right thereof.
Figure 7:
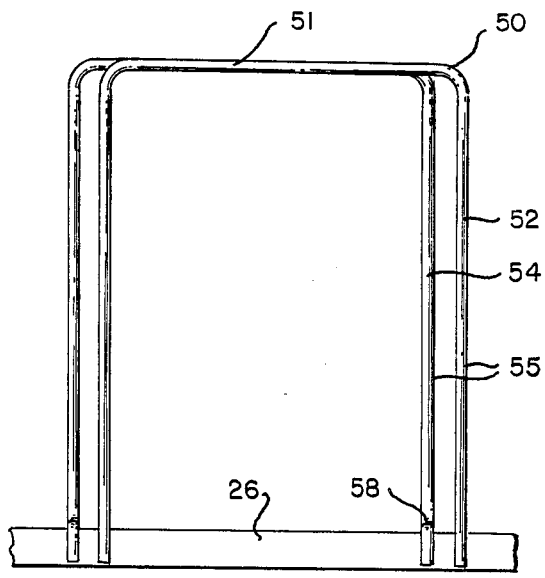
FIG. 7 is a partial section view of the rack taken along the line VII—VII of FIG. 2.
Figure 8:
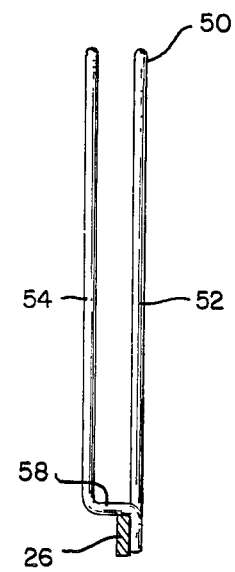
FIG. 8 is an end elevational view of the rack shown in FIG. 7.
Figure 12:
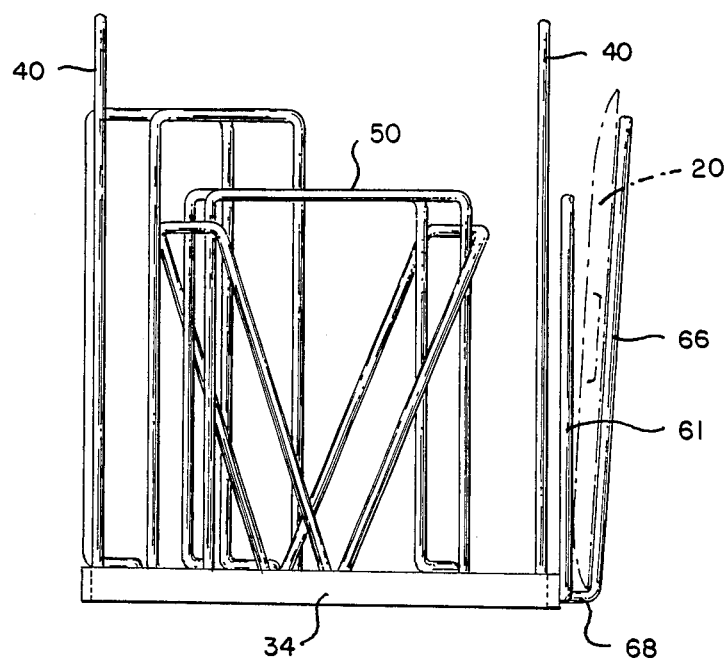
FIG. 12 is a side elevational view of the rack supporting the lid of the container.
Figure 9:
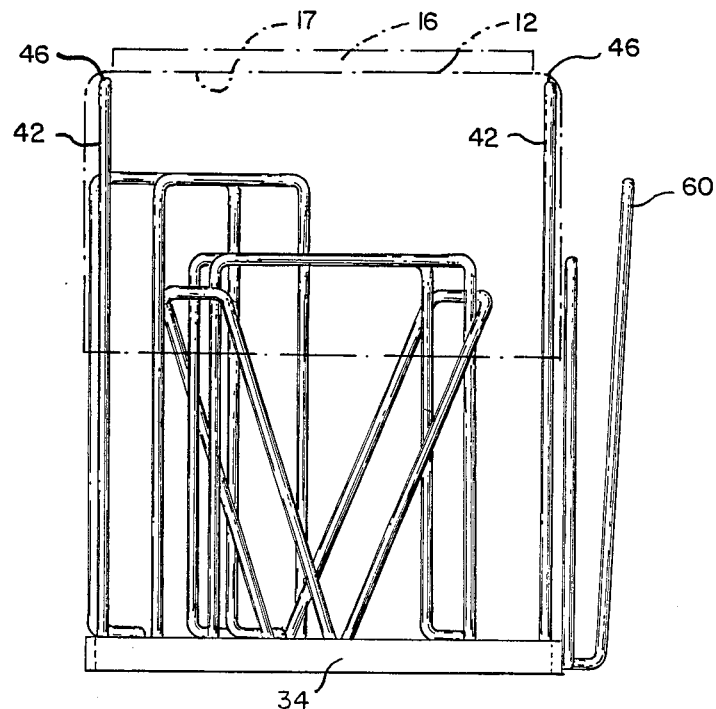
FIG. 9 is a side elevational view of the rack supporting a bottom portion of a container.
Figure 10:
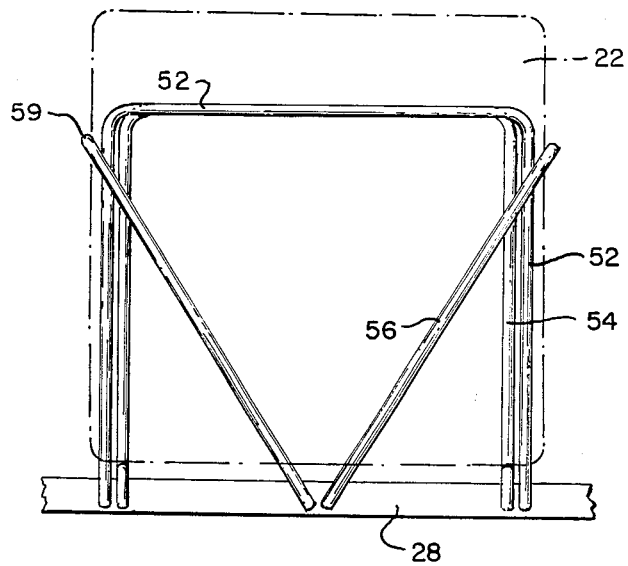
FIG. 10 is a view taken along the line V—V showing the intermediate portion of a container.
Figure 11:
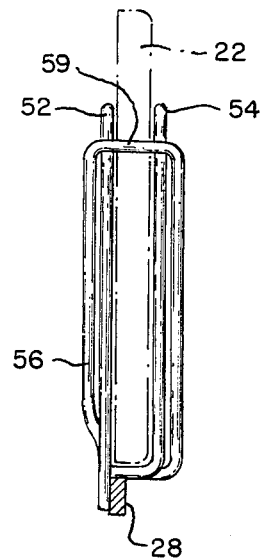
FIG. 11 is a side elevational view of the view in FIG. 10.

FIGS. 1 through 12 illustrate the preferred embodiment of the improved wire rack 10 of the present invention.

The rack 10 is designed to hold commercially available second containers 12 and first containers 14. Both sizes of containers, 12 and 14, are available in varying depths and both sizes have substantially equal widths. The second container 12 is about half the length of the first container 14.

The rack 10 is held in a commercially available basket (not shown) which is inserted into the washing and/or sterilizing apparatus. The containers 12 and 14 are adapted for holding a tray of instruments, such as surgical instruments, in their bottom portions 16 and 18. The basket simultaneously holds both the instrument tray and the rack 10 in a side-by-side, horizontally spaced relationship with respect to each other. The rack 10 should be proportioned, therefore, to fit easily within the commercially available baskets allowing sufficient space within the basket for the instrument tray so that the rack 10 can be readily used with existing health care related equipment.

The small container 12 includes bottom portion 16, shallow lid 20 and intermediate portion 22. The intermediate portions of the small and large containers 12 and 14, can be either a filter plate assembly or a valve plate assembly. The containers are designed to use either plate, alternatively. The large container 14 includes deep bottom portion 18, shallow lid 39 and intermediate portion 24. Both bottom portions 16 and 18 include bottom surfaces 17. A chamber is defined by the bottom portions 16 and 18 and enclosed by the appropriate lid 20 or 39. The intermediate portions 22 and 24 are inserted into the chamber.

Rack 10 includes a rigid rectangular frame 30 having two opposing long sides 32 and two opposing shorter sides 34. The sides 32 and 34 of frame 30 define an opening 36. An imaginary transverse axis 38 bisects frame 30 to define two halves 35. Frame 30 lies in a plane. The frame 30 should be sufficiently rigid and weighty to lower the center of gravity of the rack 10 and containers 12 or 14 held therein in order to prevent the rack 10 from becoming top heavy and the frame 30 from twisting.

A substantially diagonal member 26 crosses rectangular opening 36 of frame 30. Two skewed diagonal members 28 cross squares 35. One such diagonal member 28 is positioned substantially on each side of axis 38 of frame 30 substantially within each square 35.

Rack 10 includes a first set of wire components 40 for holding the bottom portions 16 and 18. Each component 40 includes two legs 42 and a cross member 44. Each leg 42 is connected by any suitable known means, preferably welding, at ends 48 to the long sides 32 of frame 30. The tops of legs 42 form upwardly extended curved sections 46, each of which slants downwardly toward the ends of cross member 44. There are four components 40 in the preferred embodiment of rack 10. Two components 40 are connected, side by side, on opposite sides of axis 38 on each long side 32 directly opposite the other two components 40. A first container bottom portion 18 rests in an inverted position on the curved sections 46 of the four components 40 so that the bottom portion 18 spans the opening 36. The chamber faces the opening 36. One second container bottom portion 16 can rest in a similar inverted position on the curved sections 46 of each of the two opposing components 40 so that one second container bottom portion 16 can span each square 35. Cross member 44 provides structural support for legs 42 while being maintained, by curved sections 46, in a spaced relationship relative to the bottom surfaces 17 of the bottom portions 16 or 18 to substantially reduce the surface area of the bottom portions 16 or 18 obstructed by the components 40.

The inverted position spanning at least a portion of opening 36 permits the wash fluid injected through the bottom of a conventional washer or washer-sterilizer to reach the interior surfaces of the chamber formed by bottom portions 16 or 18. Top and side sources of fluid present in some washers or washer-sterilizers can reach the exterior surfaces of the bottom portions 16 or 18. The reduced contact between bottom surfaces 17, and components 40 provided by curved sections 46 enhances the accessability of the container surfaces to the fluid.

A second set of wire components 50 for holding the intermediate portions 22 and 24 of containers 12 and 14 are connected by any suitable known means, preferably welding, to diagonal members 26 and 28. Diagonal members 28 have disposed thereon the components 50 for holding the second container intermediate portions 22. The diagonal member 26 has disposed thereon the components 50 for holding one first container intermediate portion 24.

Each component 50 includes a first support member 52 and a second support member 54. Second support members 54 include two finger like extensions 58 which extend generally horizontally relative to the plane from diagonal members 26 and 28, and bend at approximately right angles to the substantially vertical legs 55 of support member 54. Legs 55 are joined by a horizontal section 51. The first support member 52 has substantially vertical legs 55 which are directly connected to the diagonal members 26 or 28 at one end, and joined by a horizontal section 51 at the opposite end.

The components 50 disposed on diagonal members 28 may each include two third support members 56. Each support member 56 includes a substantially horizontal finger 58 extending from diagonal member 28 which bends at approximately a right angle to a leg 49 which rises angularly relative to the diagonal member 28, then bends again at an approximate right angle to a generally horizontal section 59 which bends again at an approximate right angle to a second leg 49, parallel to the first leg 49, which is connected to the other side of diagonal member 28. The two support members 56 preferably form equal but oppositely directed angles relative to the plane in which frame 30 lies so that a V-shaped configuration is achieved. The intermediate portion 22 rests on fingers 58 between support members 52 and 54 and are thereby maintained in a spaced relationship relative to the diagonal member 28 and in a substantially vertical position relative to the plane. Horizontal sections 59 of support members 56 prevent intermediate portions 22 from sliding from between support members 52 and 54. The angular position of support members 56 minimizes the contact between the intermediate portion 22 and the support members 56.

There are two components 50 disposed on diagonal member 26. They do not include support members 56 because intermediate portions 24 extend almost the entire length of diagonal member 26 and are kept from sliding by member 40. Intermediate portions 24 rest on four fingers 58, two for each component 50.

Legs 42 of components 40 are long enough so that the bottom surfaces 17 of bottom portions 16 or 18 are in a spaced relationship relative to the intermediate portions 22 or 24 when both portions 16 or 18 and 22 or 24 are being supported by rack 10. Legs 42 are preferably of equal length so that the bottom portions are supported in a substantially horizontal position relative to the plane.

The arrangement permits an efficient use of the available space in the basket and in the washing and/or sterilizing apparatus, while avoiding contact between the portions of the containers 12 or 14. The fluid injected through the bottom of the washer or washer-sterilizer through the basket contacts the intermediate portions through opening 36 of rack 10. The vertical position of the intermediate portions 22 and 24 reduces the surface area of the bottom portions 16 and 18 that is obstructed by intermediate portions 22 and 24, thereby exposing more surface area to the flow of fluid in the washer or washer-sterilizer. A slightly slanted position would permit generally the same space utilization and would not cause much obstruction to fluid flow. The greater the slant of the intermediate portions 22 and 24, however, the more surface area of the bottom portions 16 or 18 that is obstructed from efficient fluid flow. Accordingly, the substantially vertical position is preferred.

A third set of components 60 for supporting the lids 20 and 39 is connected by any suitable known means to frame 30. Each component 60 includes a fourth support member 62 and a fifth support member 64. Each fourth support member 62 has legs 61 and a horizontal section 63. Each fifth support member 64 has legs 66, fingers 68 and a horizontal section 67.

There are two components 60 on one long side 32 of frame 30. Two second container 12 lids 20 or one large container 14 lid 39 can be supported on one long side 32. It should be appreciated however, that a component 60 may be placed on one or both of the shorter sides 34 or on one or both of the longer sides 32, depending upon the available space within the basket and the washer or washer-sterilizer of choice, without exceeding the scope of the claimed invention.

Fourth support member 62 maintains the lids 20 and 39 in a spaced relationship relative to the bottom portions 16 or 18 when the bottom portions 16 or 18 are supported on components 40. Legs 61 are each connected at one end to a long side 32 and are joined by horizontal section 63.

Fifth support members 64 hold the lids 20 and 39 between fourth support members 62 and legs 66 of fifth support members 64. Fingers 68 are connected to side 32 of frame 30 and slope downwardly at a slight angle relative to the plane. Legs 66 rise upwardly from fingers 68 and horizontal sections 67 span the legs 66 of each fifth support member 64. Lids 20 and 39 rest on fingers 68 and against legs 66 to assume a substantially obtusely angular position relative to frame 30. The angle should preferably be such that the lids 20 are only slightly tilted from the vertical with the interior surface facing away from the rack 10 so that liquid is not retained in the curve of the shallow lids 20 and 39 during washing.

What is claimed is:

1. In a rack for holding at least one of either a first sized or a second sized rigid container within a basket of a predetermined size for insertion into apparatus for washing, sterilizing or both, where fluid is directed toward the containers through the basket from at least the bottom of the apparatus and each container includes a deep bottom portion defining a chamber, a shallow lid for enclosing the chamber, and an intermediate portion for insertion into the chamber, and where the basket also holds a tray of instruments of a predetermined size for subsequent insertion into the bottom portion of the container, the improvement comprising:

a rigid frame lying in a horizontal plane relative to the bottom of the apparatus and defining an opening, said frame having at least one substantially diagonal member crossing said opening;

a first set of wire components supported by said frame, said first set of components being positioned to support at least one of either the first or second container bottom portions in such an inverted position in a spaced relationship relative to said frame over at least a portion of said opening that the chamber can be exposed to the fluid directed from the bottom of the apparatus and can be positioned to prevent the retention of fluid within the bottom portions;

a second set of wire components disposed along said at least one diagonal member of said frame, said second set of wire components being positioned to support at least one of either of the first or second container intermediate portions in such a substantially vertical position relative to said plane in a spaced relationship beneath the bottom portion when a bottom portion is supported by said first set of components, that the retention of fluid in the intermediate portions is substantially prevented; and a third set of wire components supported by said frame, said third set of components being positioned to support at least one of either of the first or second component lids in such a substantially obtusely angular position relative to said frame that the retention of fluid in the lids can be substantially prevented, and positioned in such a spaced relationship relative to the bottom portions and the intermediate portions when the portions are supported in said first and second sets of components, respectively, that the direction of fluid from the bottom of the apparatus toward the chambers and the intermediate portions is unobstructed by the lids.

2. The improved rack recited in claim 1 wherein said frame and said first, second and third sets of components are positioned with respect to each other that said frame and said sets of components can be positioned within the basket in a horizontally spaced relationship relative to the tray of instruments.

3. In a rack for holding at least one of either a first sized or a second sized rigid container within a basket of a predetermined size for insertion into apparatus for washing, sterilizing or both, where fluid is directed toward the containers through the basket from at least the bottom of the apparatus and each container includes a deep bottom portion defining a chamber, a shallow lid for enclosing the chamber, and an intermediate portion for insertion into the chamber, and where the basket also holds a tray of instruments of a predetermined size for subsequent insertion into the bottom portion of the container, the improvement comprising:

a rigid rectangular frame lying in a horizontal plane relative to the bottom of the apparatus and defining an opening, said frame having such a bisecting transverse axis that two halves are defined thereby, and having a first substantially diagonal member crossing said rectangular frame and two second skewed diagonal members, one of said second diagonal members crossing one of said halves;

a first set of wire components disposed along two opposing sides of said rectangular frame and configured for supporting at least one of either of the first or second container bottom portions in such an inverted position in a spaced relationship relative to said frame that the chambers can face at least a portion of said opening for exposure to the fluid directed from the bottom of the apparatus and can be positioned to prevent the retention of fluid within the bottom portions;

a second set of wire components disposed along each of said first and second diagonal members and configured for supporting the intermediate portions in such a substantially vertical position relative to said plane in a spaced relationship relative to the bottom portion when the bottom portion is supported by said first set of components that the retention of fluids in the intermediate portions is substantially prevented, said first diagonal member having disposed thereon components of said second set for supporting the intermediate portions of either the second or first containers, and each of said second diagonal members having disposed thereon components of said second set for supporting the intermediate portion of a first container; and a third set of wire components disposed along said frame and configured for supporting at least one of either of the first or second container lids in such a substantially obtusely angular position relative to said frame that the retention of fluids in the lids can be substantially prevented, and in such a spaced relationship relative to the bottom portions and the intermediate portions when the portions are supported by said first and second sets of components, respectively, that the direction of fluid from the bottom of the apparatus toward the chambers and the intermediate portions is unobstructed by the lids.

4. In a rack for holding at least one of either a first sized or a second sized rigid container within a basket of a predetermined size for insertion into apparatus for washing, sterilizing or both, where fluid is directed toward the containers through the basket from at least the bottom of the apparatus and each container includes a deep bottom portion defining a chamber, a shallow lid for enclosing the chamber, and an intermediate portion for insertion into the chamber, and where the basket also holds a tray of instruments of a predetermined size for subsequent insertion into the bottom portion of the container, the improvement comprising:

a rigid frame lying in a horizontal plane relative to the bottom of the apparatus and defining an opening;

a first set of wire components supported by said frame, said first set of components being positioned to support at least one of either the first or second container bottom portions in such an inverted position in a spaced relationship relative to said frame over at least a portion of said opening that the chamber can be exposed to the fluid directed from the bottom of the apparatus and can be positioned to prevent the retention of fluid within the bottom portions;

said components of said first set having two legs and a cross member therebetween, said legs being substantially vertical relative to said plane and said cross member being substantially horizontal relative to said legs, each of said legs having a first end connected to one length of said frame and a second opposing end having such an upwardly extending section for contacting the bottom portions that said cross member is maintained in a spaced relationship relative to the bottom portion;

a second set of wire components supported by said frame, said second set of wire components being positioned to support at least one of either of the first or second container intermediate portions in such a substantially vertical position relative to said plane in a spaced relationship beneath the bottom portion when a bottom portion is supported by said first set of components, that the retention of fluid in the intermediate portions is substantially prevented; and a third set of wire components supported by said frame, said third set of components being positioned to support at least one of either of the first or second component lids in such a substantially obtusely angular position relative to said frame that the retention of fluid in the lids can be substantially prevented, and positioned in such a spaced relationship relative to the bottom portions and the intermediate portions when the portions are supported in said first and second sets of components, respectively, that the direction of fluid from the bottom of the apparatus toward the chambers and the intermediate portions is unobstructed by the lids;

said frame and said first, second and third sets of components being so positioned with respect to each other that said frame and said sets of components can be positioned within the basket in a horizontally spaced relationship relative to the tray of instruments.

5. The improved rack recited in claim 3 wherein each of said components of said second set has a first support member and a second support member for maintaining an intermediate portion therebetween, at least one of said support members having a first means for maintaining the intermediate portion in a spaced relationship relative to said diagonal members.

6. The improved rack recited in claim 5 wherein each of said components of said second set on said second diagonal members further comprises two third support members for maintaining the intermediate portion of a second container between said first and second support members, each of said third support members having a second means for maintaining the intermediate portion in a spaced relationship relative to the one of said second diagonal members on which said third support member is disposed, and each of said third support members being positioned in such opposing angular positions relative to said plane that said third support members form a V-shaped configuration.

7. The improved rack recited in claim 3 wherein each of said components of said third set has a fourth support member for maintaining the lid in a spaced relationship relative to the bottom portions and the intermediate portions when the bottom and intermediate portions are supported by said first and second sets of components, respectively, and a fifth support member having at least two extended fingers connected to said frame, said fifth support member and said fingers being positioned to support the lids in said substantially obtusely angular position.

8. The improved rack recited in claim 3 wherein said first set of components support the bottom portions in a substantially horizontal position relative to said plane.

9. The improved rack recited in claim 3 wherein the rack is proportioned to hold either two first containers, each of the first containers spanning one of said halves, or one second container spanning said opening.

* * * * *